United States Patent
Yoe et al.

(10) Patent No.: US 7,862,495 B2
(45) Date of Patent: Jan. 4, 2011

(54) RADIATION OR DRUG DELIVERY SOURCE WITH ACTIVITY GRADIENT TO MINIMIZE EDGE EFFECTS

(75) Inventors: Brandon James Yoe, Mountain View, CA (US); Arthur Au, Mountain View, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 193 days.

(21) Appl. No.: 09/872,135

(22) Filed: May 31, 2001

(65) Prior Publication Data

US 2002/0183581 A1    Dec. 5, 2002

(51) Int. Cl.
*A61N 5/00*    (2006.01)
(52) U.S. Cl. .................... 600/3; 623/1.15; 623/1.42
(58) Field of Classification Search .............. 600/3, 600/1, 7, 8; 623/1.42, 1.21, 1.15, 1.39; 604/103; 606/194, 195; 376/156; 427/2.25
See application file for complete search history.

(56) References Cited

U.S. PATENT DOCUMENTS

| | | | | |
|---|---|---|---|---|
| 2,072,303 A | 3/1937 | Herrmann et al. | ........ | 128/335.5 |
| 4,733,665 A | 3/1988 | Palmaz | ........ | 128/343 |
| 4,800,882 A | 1/1989 | Gianturco | ........ | 128/343 |
| 4,886,062 A | 12/1989 | Wiktor | ........ | 128/343 |
| 4,931,287 A | 6/1990 | Bae et al. | ........ | 424/484 |
| 4,977,901 A | 12/1990 | Ofstead | ........ | 128/772 |
| 4,994,560 A | 2/1991 | Kruper, Jr. et al. | ........ | 534/10 |
| 5,040,548 A | 8/1991 | Yock | ........ | 128/898 |
| 5,059,166 A * | 10/1991 | Fischell et al. | ........ | 600/3 |
| 5,064,435 A | 11/1991 | Porter | ........ | 623/12 |
| 5,087,244 A | 2/1992 | Wolinsky et al. | | |
| 5,100,429 A | 3/1992 | Sinofsky et al. | ........ | 606/195 |
| 5,213,561 A | 5/1993 | Weinstein et al. | ........ | 600/7 |
| 5,229,172 A | 7/1993 | Cahalan et al. | ........ | 427/536 |
| 5,232,444 A | 8/1993 | Just et al. | | |
| 5,258,419 A | 11/1993 | Rolando et al. | ........ | 522/109 |
| 5,278,200 A | 1/1994 | Coury et al. | ........ | 523/112 |
| 5,308,641 A | 5/1994 | Cahalan et al. | ........ | 427/2 |
| 5,328,471 A | 7/1994 | Slepian | ........ | 604/101 |
| 5,336,518 A | 8/1994 | Narayanan et al. | ........ | 623/1 |
| 5,342,283 A | 8/1994 | Good | ........ | 600/8 |

(Continued)

FOREIGN PATENT DOCUMENTS

DE    19916086    10/1999

(Continued)

OTHER PUBLICATIONS

Kay et al, The pattern of restenosis and vascular remodelling after cold-end radioactive stent implantation, European Heart Journal, vol. 2001, issue 22, pp. 1311-1317 & 1245-1247.*

(Continued)

*Primary Examiner*—Patricia M Bianco
*Assistant Examiner*—Camtu T Nguyen
(74) *Attorney, Agent, or Firm*—Squire, Sanders & Dempsey, L.L.P.

(57) ABSTRACT

A radiation delivery source, such as a stent, and method for making radioactive a delivery source are disclosed. A drug delivery source and method for making a drug delivery region on the drug delivery source are also disclosed.

21 Claims, 10 Drawing Sheets

U.S. PATENT DOCUMENTS

| | | | | |
|---|---|---|---|---|
| 5,342,621 A | 8/1994 | Eury | 424/423 |
| 5,344,455 A | 9/1994 | Keogh et al. | 623/11 |
| 5,350,800 A | 9/1994 | Verhoeven et al. | 525/54.2 |
| 5,366,504 A | 11/1994 | Andersen et al. | 623/11 |
| 5,399,352 A * | 3/1995 | Hanson | 424/423 |
| 5,411,466 A | 5/1995 | Hess | 600/3 |
| 5,415,938 A | 5/1995 | Cahalan et al. | 428/409 |
| 5,429,618 A | 7/1995 | Keogh | 604/266 |
| 5,443,496 A | 8/1995 | Schwartz et al. | 623/1 |
| 5,464,450 A | 11/1995 | Buscemi et al. | 623/6 |
| 5,464,650 A | 11/1995 | Berg et al. | 427/2.3 |
| 5,470,313 A | 11/1995 | Crocker et al. | |
| 5,476,509 A | 12/1995 | Keogh et al. | 623/1 |
| 5,500,013 A | 3/1996 | Buscemi et al. | 623/1 |
| 5,551,954 A | 9/1996 | Buscemi et al. | 623/1 |
| 5,554,182 A | 9/1996 | Dinh et al. | 623/1 |
| 5,571,166 A | 11/1996 | Dinh et al. | 623/1 |
| 5,578,073 A | 11/1996 | Haimovich et al. | 623/1 |
| 5,591,224 A | 1/1997 | Schwartz et al. | 623/1 |
| 5,591,227 A | 1/1997 | Dinh et al. | 623/1 |
| 5,599,352 A | 2/1997 | Dinh et al. | 623/1 |
| 5,605,696 A | 2/1997 | Eury et al. | 424/423 |
| 5,624,411 A | 4/1997 | Tuch | 604/265 |
| 5,628,730 A | 5/1997 | Shapland et al. | 604/21 |
| 5,628,785 A | 5/1997 | Schwartz et al. | 623/1 |
| 5,637,113 A | 6/1997 | Tartaglia et al. | 623/1 |
| 5,649,951 A | 7/1997 | Davidson | 606/198 |
| 5,649,977 A | 7/1997 | Campbell | 623/1 |
| 5,667,767 A | 9/1997 | Greff et al. | 424/9.411 |
| 5,670,558 A | 9/1997 | Onishi et al. | 523/112 |
| 5,674,242 A | 10/1997 | Phan et al. | 606/198 |
| 5,693,085 A | 12/1997 | Buirge et al. | 623/1 |
| 5,693,376 A | 12/1997 | Fetherston et al. | 427/523 |
| 5,697,967 A | 12/1997 | Dinh et al. | 623/1 |
| 5,700,286 A | 12/1997 | Tartaglia et al. | 623/1 |
| 5,702,818 A | 12/1997 | Cahalan et al. | 428/409 |
| 5,707,385 A | 1/1998 | Williams | 606/192 |
| 5,711,812 A | 1/1998 | Chapek et al. | 118/723 E |
| 5,713,949 A | 2/1998 | Jayaraman | 623/1 |
| 5,716,981 A | 2/1998 | Hunter et al. | 514/449 |
| 5,722,984 A | 3/1998 | Fischell et al. | 606/198 |
| 5,730,698 A | 3/1998 | Fischell et al. | 600/3 |
| 5,766,710 A | 6/1998 | Turnlund et al. | 428/36.1 |
| 5,769,883 A | 6/1998 | Buscemi et al. | 623/1 |
| 5,769,884 A | 6/1998 | Solovay | 623/1 |
| 5,782,742 A * | 7/1998 | Crocker et al. | 600/3 |
| 5,800,392 A | 9/1998 | Racchini | 604/96 |
| 5,810,873 A | 9/1998 | Morales | 606/198 |
| 5,811,151 A | 9/1998 | Hendriks et al. | 427/2.24 |
| 5,824,048 A | 10/1998 | Tuch | 623/1 |
| 5,824,049 A | 10/1998 | Ragheb et al. | 623/1 |
| 5,826,586 A | 10/1998 | Mishra et al. | 128/898 |
| 5,830,178 A | 11/1998 | Jones et al. | 604/49 |
| 5,837,313 A | 11/1998 | Ding et al. | 427/2.21 |
| 5,840,009 A | 11/1998 | Fischell et al. | |
| 5,843,172 A | 12/1998 | Yan | 623/1 |
| 5,851,508 A | 12/1998 | Greff et al. | 424/9.411 |
| 5,857,998 A | 1/1999 | Barry | 604/96 |
| 5,858,556 A | 1/1999 | Eckert et al. | 428/586 |
| 5,858,990 A | 1/1999 | Walsh | 514/44 |
| 5,865,814 A | 2/1999 | Tuch | 604/265 |
| 5,866,113 A | 2/1999 | Hendriks et al. | 424/78.17 |
| 5,871,436 A | 2/1999 | Eury | 600/3 |
| 5,871,437 A | 2/1999 | Alt | 600/3 |
| 5,873,904 A | 2/1999 | Ragheb et al. | 623/1 |
| 5,893,840 A | 4/1999 | Hull et al. | 604/96 |
| 5,897,911 A | 4/1999 | Loeffler | 427/2.25 |
| 5,898,178 A * | 4/1999 | Bunker | 250/423 R |
| 5,902,631 A | 5/1999 | Wang et al. | 427/2.1 |
| 5,916,234 A | 6/1999 | Lam | 606/198 |
| 5,925,552 A | 7/1999 | Keogh et al. | 435/174 |
| 5,928,916 A | 7/1999 | Keogh | 435/174 |
| 5,947,993 A | 9/1999 | Morales | 606/198 |
| 5,951,881 A | 9/1999 | Rogers et al. | 216/41 |
| 5,968,091 A | 10/1999 | Pinchuk et al. | 623/1 |
| 5,968,092 A | 10/1999 | Buscemi et al. | 623/1 |
| 5,971,954 A | 10/1999 | Conway et al. | 604/96 |
| 5,972,027 A | 10/1999 | Johnson | 623/1 |
| 5,972,029 A | 10/1999 | Fuisz | 623/1 |
| 5,980,564 A | 11/1999 | Stinson | 623/1 |
| 5,980,928 A | 11/1999 | Terry | 424/427 |
| 5,980,972 A | 11/1999 | Ding | 427/2.24 |
| 5,997,517 A | 12/1999 | Whitbourne | 604/265 |
| 6,010,530 A | 1/2000 | Goicoechea | 623/1 |
| 6,013,099 A | 1/2000 | Dinh et al. | 623/1 |
| 6,015,541 A | 1/2000 | Greff et al. | 424/1.25 |
| 6,019,789 A | 2/2000 | Dinh et al. | 623/1 |
| 6,024,918 A | 2/2000 | Hendriks et al. | 422/44 |
| 6,027,526 A | 2/2000 | Limon et al. | 623/1 |
| 6,033,719 A | 3/2000 | Keogh | 427/2.12 |
| 6,042,606 A | 3/2000 | Frantzen | 623/1 |
| 6,042,875 A | 3/2000 | Ding et al. | 427/2.24 |
| 6,059,752 A * | 5/2000 | Segal | 604/107 |
| 6,071,305 A | 6/2000 | Brown et al. | 623/1 |
| 6,080,099 A * | 6/2000 | Slater et al. | 600/8 |
| 6,080,190 A | 6/2000 | Schwartz | 623/1 |
| 6,093,199 A | 7/2000 | Brown et al. | 606/200 |
| 6,096,070 A | 8/2000 | Ragheb et al. | 623/1 |
| 6,099,455 A | 8/2000 | Columbo et al. | |
| 6,099,559 A | 8/2000 | Nolting | 623/1.16 |
| 6,099,561 A | 8/2000 | Alt | 623/1.44 |
| 6,106,454 A | 8/2000 | Berg et al. | 600/3 |
| 6,110,483 A | 8/2000 | Whitbourne et al. | 424/423 |
| 6,140,127 A | 10/2000 | Sprague | 435/395 |
| 6,140,431 A | 10/2000 | Kinker et al. | 526/79 |
| 6,149,574 A * | 11/2000 | Trauthen et al. | 600/3 |
| 6,153,252 A | 11/2000 | Hossainy et al. | 427/2.3 |
| 6,165,212 A | 12/2000 | Dereume et al. | 623/1.13 |
| 6,168,619 B1 | 1/2001 | Dinh et al. | 623/1.13 |
| 6,203,551 B1 | 3/2001 | Wu | 606/108 |
| 6,214,901 B1 | 4/2001 | Chudzik et al. | 523/113 |
| 6,224,894 B1 | 5/2001 | Jamiolkowski et al. | 424/426 |
| 6,231,590 B1 | 5/2001 | Slaikeu et al. | 606/200 |
| 6,242,041 B1 | 6/2001 | Katoot et al. | 427/2.24 |
| 6,253,443 B1 | 7/2001 | Johnson | 29/557 |
| 6,254,632 B1 | 7/2001 | Wu et al. | 623/1.15 |
| 6,258,121 B1 | 7/2001 | Yang et al. | 623/1.46 |
| 6,262,034 B1 | 7/2001 | Mathiowitz et al. | 514/44 |
| 6,273,850 B1 * | 8/2001 | Gambale et al. | 600/3 |
| 6,273,913 B1 | 8/2001 | Wright et al. | 623/1.42 |
| 6,287,628 B1 | 9/2001 | Hossainy et al. | 427/2.3 |
| 6,296,603 B1 * | 10/2001 | Turnlund et al. | 600/3 |
| 6,319,520 B1 | 11/2001 | Wuthrich et al. | 424/482 |
| 4,733,665 C2 | 1/2002 | Palmaz | 606/108 |
| 6,344,035 B1 | 2/2002 | Chudzik et al. | 604/265 |
| 6,379,379 B1 | 4/2002 | Wang | 623/1.31 |
| 6,379,381 B1 | 4/2002 | Hossainy et al. | 623/1.42 |
| 6,413,272 B1 | 7/2002 | Igaki | 623/1.15 |
| 6,481,262 B2 | 11/2002 | Ching et al. | 72/416 |
| 6,488,701 B1 | 12/2002 | Nolting et al. | 623/1.13 |
| 6,504,307 B1 * | 1/2003 | Malik et al. | 315/111.21 |
| 6,510,722 B1 | 1/2003 | Ching et al. | 72/402 |
| 6,524,232 B1 * | 2/2003 | Tang et al. | 600/3 |
| 6,554,758 B2 * | 4/2003 | Turnlund et al. | 600/3 |
| 6,558,733 B1 | 5/2003 | Hossainy et al. | 427/2.24 |
| 6,582,417 B1 * | 6/2003 | Ledesma et al. | 604/529 |
| 6,596,296 B1 | 7/2003 | Nelson et al. | 424/426 |
| 6,605,114 B1 | 8/2003 | Yan et al. | 623/1.43 |
| 6,656,216 B1 | 12/2003 | Hossainy et al. | 623/1.13 |
| 6,663,662 B2 | 12/2003 | Pacetti et al. | 623/1.13 |
| 6,699,281 B2 | 3/2004 | Vallana et al. | 623/1.42 |
| 6,764,505 B1 | 7/2004 | Hossainy et al. | 623/1.15 |
| 6,783,793 B1 * | 8/2004 | Hossainy et al. | 427/2.25 |
| 6,861,088 B2 | 3/2005 | Weber et al. | |

| | | | |
|---|---|---|---|
| 6,865,810 | B2 | 3/2005 | Stinson |
| 6,869,443 | B2 | 3/2005 | Buscemi et al. |
| 6,878,160 | B2 | 4/2005 | Gilligan et al. |
| 6,887,270 | B2 | 5/2005 | Miller et al. |
| 6,887,485 | B2 | 5/2005 | Fitzhugh et al. |
| 6,890,546 | B2 | 5/2005 | Mollison et al. |
| 6,899,731 | B2 | 5/2005 | Li et al. |
| 6,908,480 | B2 * | 6/2005 | Jayaraman .................. 623/1.42 |
| 2001/0001806 | A1 * | 5/2001 | Turnlund et al. ............... 600/3 |
| 2002/0183581 | A1 | 12/2002 | Yoe et al. ........................ 600/3 |
| 2005/0037052 | A1 | 2/2005 | Udipi et al. |
| 2005/0038134 | A1 | 2/2005 | Loomis et al. |
| 2005/0038497 | A1 | 2/2005 | Neuendorf et al. |
| 2005/0043786 | A1 | 2/2005 | Chu et al. |
| 2005/0049693 | A1 | 3/2005 | Walker |
| 2005/0049694 | A1 | 3/2005 | Neary |
| 2005/0054774 | A1 | 3/2005 | Kangas |
| 2005/0055044 | A1 | 3/2005 | Kangas |
| 2005/0055078 | A1 | 3/2005 | Campbell |
| 2005/0060020 | A1 | 3/2005 | Jenson |
| 2005/0064088 | A1 | 3/2005 | Fredrickson |
| 2005/0065501 | A1 | 3/2005 | Wallace |
| 2005/0065545 | A1 | 3/2005 | Wallace |
| 2005/0065593 | A1 | 3/2005 | Chu et al. |
| 2005/0074406 | A1 | 4/2005 | Couvillon, Jr. et al. |
| 2005/0074545 | A1 | 4/2005 | Thomas |
| 2005/0075714 | A1 | 4/2005 | Cheng et al. |
| 2005/0079274 | A1 | 4/2005 | Palasis et al. |
| 2005/0084515 | A1 | 4/2005 | Udipi et al. |
| 2005/0106210 | A1 | 5/2005 | Ding et al. |
| 2005/0113903 | A1 | 5/2005 | Rosenthal et al. |

FOREIGN PATENT DOCUMENTS

| | | |
|---|---|---|
| EP | 0 627 226 | 12/1994 |
| EP | 0665023 | 8/1995 |
| EP | 0 701 803 | 3/1996 |
| EP | 0 850 604 | 7/1998 |
| EP | 0 972 498 | 1/2000 |
| EP | 0970711 | 1/2000 |
| EP | 0 850 651 | 6/2000 |
| EP | 1 103 234 | 5/2001 |
| WO | WO 90/01969 | 3/1990 |
| WO | WO91/12846 | 9/1991 |
| WO | WO97/45105 | 12/1997 |
| WO | WO 98/23228 | 6/1998 |
| WO | WO99/63981 | 12/1999 |
| WO | WO00/12147 | 3/2000 |
| WO | WO00/64506 | 11/2000 |
| WO | WO01/01890 | 1/2001 |
| WO | WO01/45763 | 6/2001 |
| WO | WO 01/91918 | 12/2001 |
| WO | WO 02/47731 | 6/2002 |

OTHER PUBLICATIONS

Barath et al., *Low Dose of Antitumor Agents Prevents Smooth Muscle Cell Proliferation After Endothelial Injury*, JACC 13(2):252A (1989) (Abstract).

Matsumaru et al., *Embolic Materials for Endovascular Treatment of Cerebral Lesions*, J. Biomater. Sci. Polymer Edn. 8(7):555-569 (1997).

Miyazaki et al., *Antitumor Effect of Implanted Ethylene-Vinyl Alcohol Copolymer Matrices Containing Anticancer Agents on Ehrlich Ascites Carcinoma and P388 Leukemia in Mice*, Chem. Pharm. Bull. 33(6):2490-2498 (1985).

Miyazawa et al., *Effects of Pemirolast and Tranilast on Intimal Thickening After Arterial Injury in the Rat*, J. Cardiovasc. Pharmacol. 30(2):157-162 (1997).

Ohsawa et al., *Preventive Effects of an Antiallergic Drug, Pemirolast Potassium, on Restenosis After Percutaneous Transluminal Coronary Angioplasty*, Am. Heart J. 136(6):1081-1087 (Dec. 1998).

Shigeno, *Prevention of Cerebrovascular Spasm by Bosentan, Novel Endothelin Receptor*, Chem. Abstracts 125:212307 (1996).

van der Giessen et al., *"Edge Effect" of $^{32}P$ Radioactive Stents is Caused by the Combination of Chronic Stent Injury and Radioactive Dose Falloff*, Circ. 104:2236-2241 (Oct. 30, 2001).

U.S. Appl. No. 09/697,106, filed Oct. 26, 2000, Hossainy et al.

U.S. Appl. No. 09/834,012, filed Apr. 12, 2001, Hossainy et al.

Fischell et al., *"Low-Dose, β-Particle Emission from 'Stent' Wire Results in Complete, Localized Inhibition of Smooth Muscle Cell Proliferation"*, Circulation, vol. 90(6):2956-2963, Dec. 1994.

Hehrlein et al., *"Low-Dose Radioactive Endovascular Stents Prevent Smooth Muscle Cell Proliferation and Neointimal Hyperplasia in Rabbits"*, Circulation, vol. 92(6):1570-1575, Sep. 15, 1995.

Liermann et al., *"Prophylactic Endovascular Radiotherapy to Prevent Intimal Hyperplasia after Stent Implantation in Femoropopliteal Arteries"*, CardioVascular and Interventional Radiology 17:12-16, 1994.

Malik et al., *Development of an Energetic Ion Assisted Mixing and Deposition Process for $TIN_x$ and Diamondlike Carbon Films, Using a Co-axial Geometry in Plasma Source Ion Implantation*, J. Vac. Sci. Technol. A 15(6):2875-2879 (Nov./Dec. 1997).

Malik et al., *Overview of Plasma Source Ion Implantation Research at University of Wisconsin-Madison*, J. Vac. Sci. Technol. B 12(2):843-849 (Mar./Apr. 1994).

Malik et al., *Sheath Dynamics and Dose Analysis for Planar Targets in Plasma Source Ion Implantation*, Plasma Sources Sci. Technol. 2:81-85 (1993).

Scheuer et al., *Model of Plasma Source Ion Implantation in Planar, Cylindrical, and Spherical Geometries*, J. Appl. Phys. 67(3):1241-1245 (Feb. 1990).

Serruys et al., *I Like the Candy, I Hate the Wrapper; the $^{32}P$ Radioactive Stent*, Circulation 101:3-7 (Jan. 2000).

Shamim et al., *Measurement of Electron Emission Due to Energetic Ion Bombardment in Plasma Source Ion Implantation*, J. Appl. Phys. 70(9):4756-4759 (Nov. 1991).

Shamim et al., *Measurements of Spatial and Temporal Sheath Evolution for Spherical and Cylindrical Geometries in Plasma Source Ion Implantation*, J. Appl. Phys. 69(5):2904-2908 (Mar. 1991).

Wiesendanger et al., *Contributions Of Scanning Probe Microscopy And Spectroscopy To The Investigation And Fabrication Of Nanometer-Scale Structures*, J. Vac. Sci. Technol. B, 12(2):515-529 (Mar./Apr. 1994).

Serruys, et al., "I Like The Candy, I Hate The Wrapper", Circulation, Jan. 2000, pp. 3-7, vol. 101, Copyright 2000, American Heart Association, Inc.

U.S. Appl. No. 09/894,293, filed Jun. 27, 2001, Roorda et al.

U.S. Appl. No. 10/177,154, filed Jun. 21, 2002, Hossainy et al.

U.S. Appl. No. 10/293,658, filed Nov. 12, 2002, Santos et al.

U.S. Appl. No. 10/835,229, filed Apr. 28, 2004, Prabhu et al.

Crowe et al., *Absorption and Intestinal Metabolism of SDZ-RAD and Rapamycin in Rats*, Drug Metabolism and Disposition, vol. 27, No. 5, pp. 627-632 (1999).

*FFS700 MSI Balloon Form/Fold/Set Equipment (PTCA), FFS800 MSI Balloon Form/Fold/Set Equipment (PTA)*, Machine Solutions, http://machinesolutions.org/ffs7_8.html, 2 pages, printed Nov. 21, 2003.

Fischell et al., *The Bx VELOCITY™ STENT* (Biocompatibles Ltd.), 5 pages (2001).

Gercken et al., *Results of the Jostent Coronary Stent Graft Implantation in Various Clinical Settings: Procedural and Follow-Up Results*, vol. 56, No. 3, pp. 353-360 (2002).

Kawai et al., *Physiologically Based Pharmacokinetics of Cyclosporine A: Extension to Tissue Distribution Kinetics in Rats and Scale-up to Human*, The Journal of Pharmacology and Experimental Therapeutics, vol. 287, No. 2, pp. 457-468 (1998).

Kovarik et al., *Pharmacokinetic and Pharmacodynamic Assessments of HMG-CoA Reductase Inhibitors When Coadministered with Everolimus*, Journal of Clinical Pharmacology, vol. 42, pp. 222-228 (2002).

Lemos et al., *Coronary Restenosis After Sirolimus-Eluting Stent Implantation*, Circulation, vol. 108, No. 3, pp. 257-260 (Jul. 22, 2003).

*SC700 MSI Stent Crimping Equipment (PTCA), SC800 MSI Stent Crimping Equipment (PTA)*, Machine Solutions, http://www.machinesolutions.org/sc7_8.html, 2 pages, printed Nov. 21, 2003.

Serkova et al., *Tissue Distribution and Clinical Monitoring of the Novel Macrolide Immunosuppressant SDZ-RAD and its Metabolites in Monkey Lung Transplant Recipients: Interaction with Cyclosporine*, The Journal of Pharmacology and Experimental Therapeutics, vol. 294, No. 1, pp. 323-332 (2000).

Zimarino et al., Analysis of Stent Edge Restenosis with Different Forms of Brachytherapy, The American Journal of Cardiology, vol. 89, pp. 322-325 (Feb. 1, 2002).

* cited by examiner

RADIATION OR DRUG DELIVERY SOURCE WITH ACTIVITY GRADIENT TO MINIMIZE EDGE EFFECTS

FIELD OF THE INVENTION

This invention relates generally to radiation and drug delivery to treat vascular lesions and, more particularly, to vascular delivery sources such as stents, source wires or catheters having radiation activity or drug concentration gradients.

BACKGROUND OF THE INVENTION

The use of radiation delivery sources such as stents or source wires to treat vascular lesions is well known in the medical field. The enhanced sensitivity of active, proliferating cells to the lethal effects of ionizing radiation prevents neointimal proliferation, vessel contraction and hyperplasia associated with restenosis following balloon dilatation procedures.

Unfortunately, vascular brachytherapy has a common side effect associated particularly with radioactive stents known as the candy-wrapper effect or edge effect, whereby tissue proliferation occurs at the extremes of the irradiated region. Vessel injury due to balloon or stent expansion and the rapid transition from radiated to non-radiated treatment regions are factors that may contribute to or cause the edge effect. It is believed that the edge effect is more severe in the presence of increased vessel injury manifested in forms such as barotraumas, expansion strains and endothelial cell denudation.

Porcine animal studies in which half-radioactive stents (radioactive only over half of their longitudinal length) were implanted in coronary arteries showed two regions of cell proliferation. Tissue proliferation was greatest in the center of the stent where the radioactivity of the stent went from a nominal value to a non-radioactive value. This type of transition also existed at the end of the radioactive portion of the stent, which also exhibited cell proliferation.

Thus, it is believed that the principal cause of the edge effect may be the occurrence of a sudden drop from high to low or zero radiation dose. Radiation delivered to a vessel, either affected or unaffected with lesions, may be interpreted as causing injury, which forces the vessel to heal. Cell proliferation and restenosis are forms of healing. Greater injury may result in greater healing responses, including cell proliferation, but increasing radiation dosage above a certain threshold may prevent such vessel healing and cell proliferation.

For example, a radiation delivery source such as a stent delivers radiation at a treatment level high enough to prevent cell proliferation. At the ends of the stent however, a short transition from a high to a low or no radiation-treated area creates a proximity of high radiation-treated and low or zero radiation-treated cells. Because cells react to injury to surrounding tissue, healthy tissue near the radiation-treated tissue reacts with unwanted cell growth. The low or zero radiation-treated tissue experiences minimal injury, but responds to the injury of the adjacent high radiation-treated tissue. In essence, there is not enough of a radiation dose delivered near the stent ends to prevent cell proliferation to surrounding tissue. Cell proliferation and restenosis may be stimulated by radiation injury to the nearby high radiation tissue even though the radiation is used initially to inhibit cell proliferation and restenosis to the lesion area.

Anti-proliferative drugs used to treat vascular lesions may also result in unwanted side effects comparable to radiation therapy. In addition to restenosis forming at the extremes of the treated region, healing and regeneration of the endothelial layer lining the cell wall may be delayed. For example, drugs selected for delivery by stents are often very toxic and potent, killing endothelial cells in the process. Endothelial cells are essential to maintain vascular homeostasis of the vessel.

Thus, what is needed is a radiation delivery apparatus and method that minimize or prevent cell proliferation at the ends of a radiation delivery source or radioactive region. A radioactivity gradient at the ends of a delivery source or region would increase the dose transition length from high to low or zero radiation. Consequently, cell proliferation from nearby tissue would be minimized or prevented. Similarly, drug gradients on drug delivery sources would prevent cell proliferation or minimize toxic effect of drugs at the ends of the delivery source and allow for a gradual, controlled healing to occur and progress into the center of the device.

SUMMARY OF THE INVENTION

Disclosed are embodiments of an apparatus and methods of making an apparatus including an elongated source of a therapeutic agent to deliver a dose of the therapeutic agent to a vessel. The source has a gradient of therapeutic agent concentrations near a proximal end and a distal end of the elongated source.

In one embodiment, an elongated radiation delivery source has a radioactive region. In another embodiment, an elongated drug delivery source has a drug region. The radioactive region or the drug region has a proximal end and a distal end. A therapeutic radioactivity level or drug concentration level exists between the proximal end and the distal end of the radioactive or drug region. The radioactive or drug region also has gradients near the proximal end and the distal end. The radioactivity or drug concentration gradients have radioactivity or drug concentrations transitioning from a therapeutic level to a non-therapeutic level. The corresponding dose to the treated area will not effectuate a sharp drop-off from therapeutic radiation exposure to no radiation or drug concentration exposure, thought to be a cause of the candy wrapper or edge effect.

BRIEF DESCRIPTION OF THE DRAWINGS

The present invention is illustrated by way of example, and not limitation, in the figures of the accompanying drawings in which.

DETAILED DESCRIPTION

Embodiments of intravascular radiation or drug delivery sources described below have longitudinal radiation or drug concentration gradients to minimize or to prevent proliferation of cells at the ends of the radiation or drug delivery source, commonly known as edge effect or candy wrapper. Cell proliferation response is believed to be caused by a very short transition area of high radiation or drug dose, corresponding to the therapeutic radioactivity or drug concentration level necessary to treat a lesion, to low or zero radiation or drug dose at the ends of a radiation or drug delivery source. By gradually decreasing radiation dose or drug dose levels by gradually reducing the radioactivity or drug concentration near the delivery source ends, the edge effect may be minimized or prevented altogether.

In one embodiment, a radiation delivery source has an identifiable radioactive region. The radioactive region has at least two radioactivity levels. The radioactive region has radioactivity gradients near the proximal end and distal end of the radiation delivery source. The gradients have radioactivity transitioning from a therapeutic radioactivity level to a non-therapeutic radioactivity level that corresponds to a radiation dose gradient absorbed by the vessel wall during treatment. The radiation delivery source may be any type known in the art including but not limited to stents, source wires and catheters. Methods for activating radiation delivery sources known in the art include but are not limited to ion beam implantation and plasma ion coating.

Figure 1:
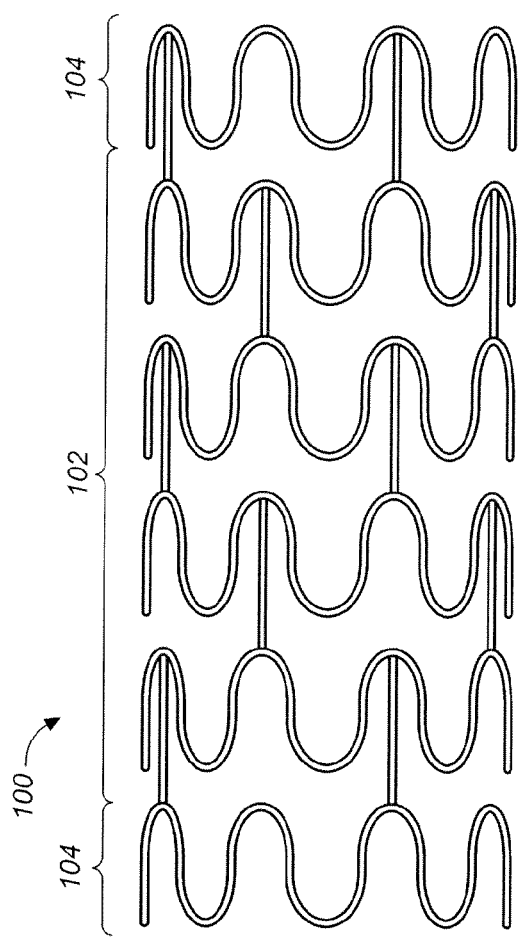
FIG. 1 is a side view of one embodiment of the present invention in which a radiation delivery source in the form of a stent has radioactivity gradients near the stent ends.

Turning now to the figures, FIG. 1 shows a side view of an embodiment of the present invention. The radiation delivery source shown in FIG. 1 is exemplified in the form of an intravascular stent. Any variety of radioactive stent configurations, including but not limited to interconnected, self-expandable or balloon-expandable, cylindrical elements or slotted tube-type designs may be delivered by practicing the invention. In FIG. 1, cylindrical stent 100 has a radioactivity region with two radioactivity levels. Central region 102 has a first radioactivity level for therapeutic purposes, such as treating a lesion in a vessel. One of the features of stent 100 is that radioactivity transitions from a therapeutic level to a non-therapeutic level within the radioactive region. The transition involves a gradient of decreasing radioactivity from the first radioactivity level that begins at a point near end regions 104. The gradients continue longitudinally towards the ends of stent 100 to achieve a second, non-therapeutic radioactivity level. The second radioactivity level is generally less than the first radioactivity level of central region 102. The radioactivity gradients prevent the treated vessel from experiencing a short, sudden change from high radiation dose to no dose at the stent ends.

Figure 2:
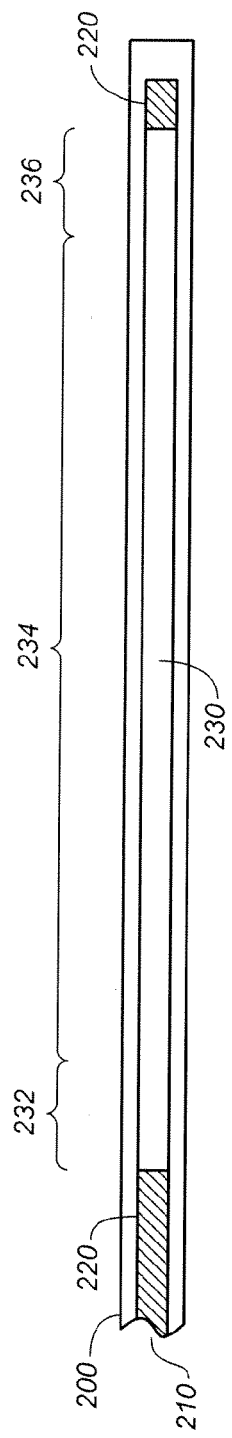
FIG. 2 is a cross-sectional, side view of one embodiment of the present invention in which a radiation delivery source in the form of a source wire has radioactivity gradients near the ends of the radioactive region of the source wire.

FIG. 2 shows a cross-sectional, side view of another embodiment of the present invention. The exemplary radiation delivery source in FIG. 2 includes radioactive source wire 210 enclosed in catheter 200. Any variety of radiation source wire configurations may be utilized by practicing the invention. In this embodiment, radiation source wire 210 includes non-radioactive region 220 and radioactive region 230. Radioactive region 230 is typically at or near the distal end of source wire 210. Central region 234 on radioactive region 230 has a first, therapeutic radioactivity level for treating a lesion in a vessel. A gradient of decreasing radioactivity from the therapeutic radioactivity level begins at points near proximal end region 232 and distal end region 236. The radioactivity gradients continue longitudinally towards both ends of radioactive region 230 to achieve a second, non-therapeutic radioactivity level. The non-therapeutic radioactivity level is generally less than the therapeutic radioactivity level of central region 234.

Figure 3:
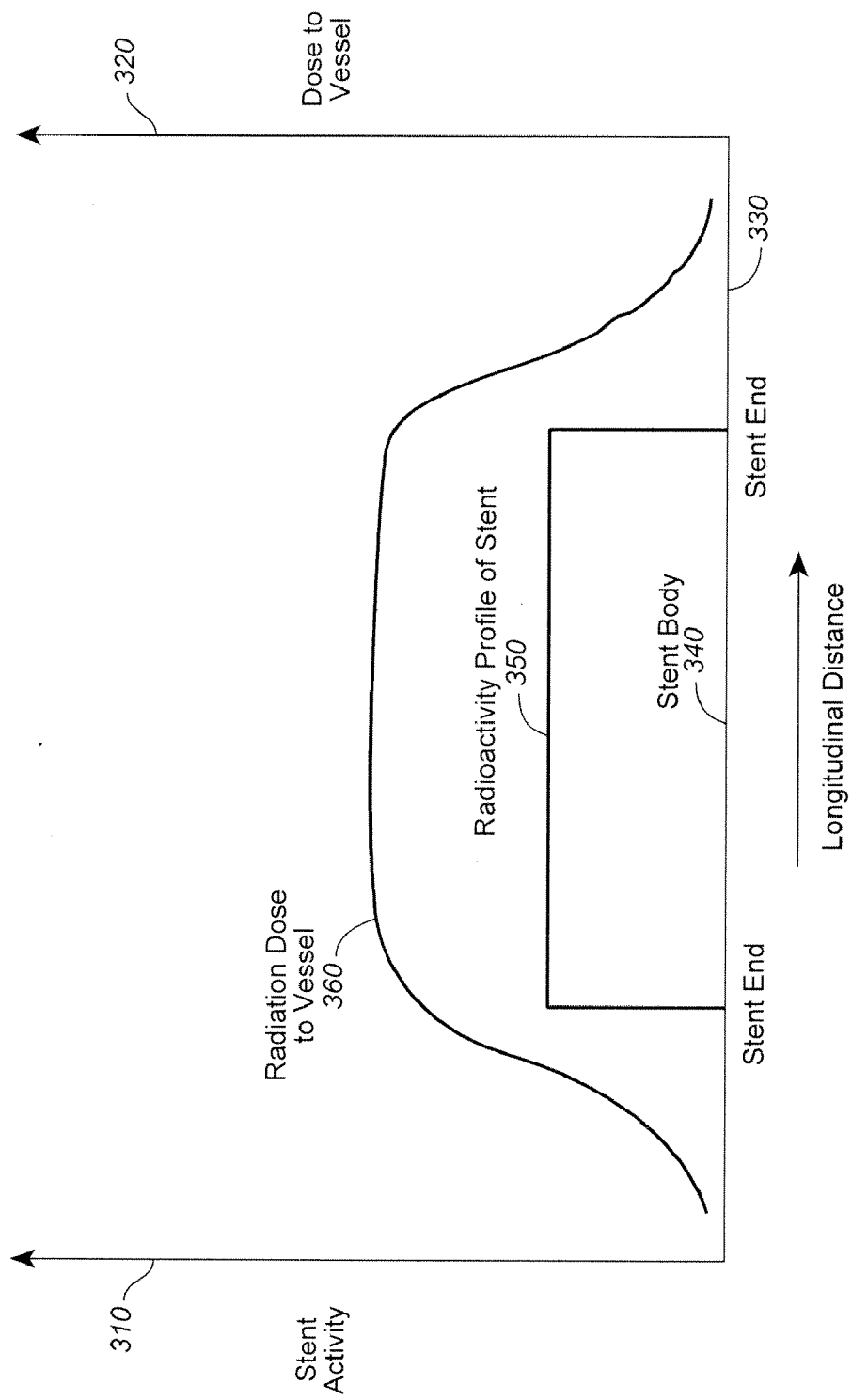
FIG. 3 is a graphical representation of typical radioactivity and radiation dose profiles of a radiation delivery source.

FIG. 3 shows a graphical representation of one example of a radiation dose profile that a radiated vessel experiences as the activity drops off at the ends of the radiation delivery source. A stent is the radiation source for purposes of explanation of FIG. 3. Left vertical axis 310 represents stent radioactivity and right vertical axis 320 represents the radiation dose from the stent to the treated vessel. Horizontal axis 330 represents the longitudinal length of the stent. Line segment 340 labeled "stent body" between the points labeled "stent end" represents the actual length of the stent on horizontal axis 330. As shown, the stent has a constant level of radioactivity 350 along its entire length, and the corresponding dose level 360 to the treated vessel is also steady throughout most of the length of the stent. Dose level 360 drops rapidly to zero near the stent ends. This rapid decrease in radiation dose is thought to cause the counter-therapeutic edge effect in a treated vessel.

Figure 4:
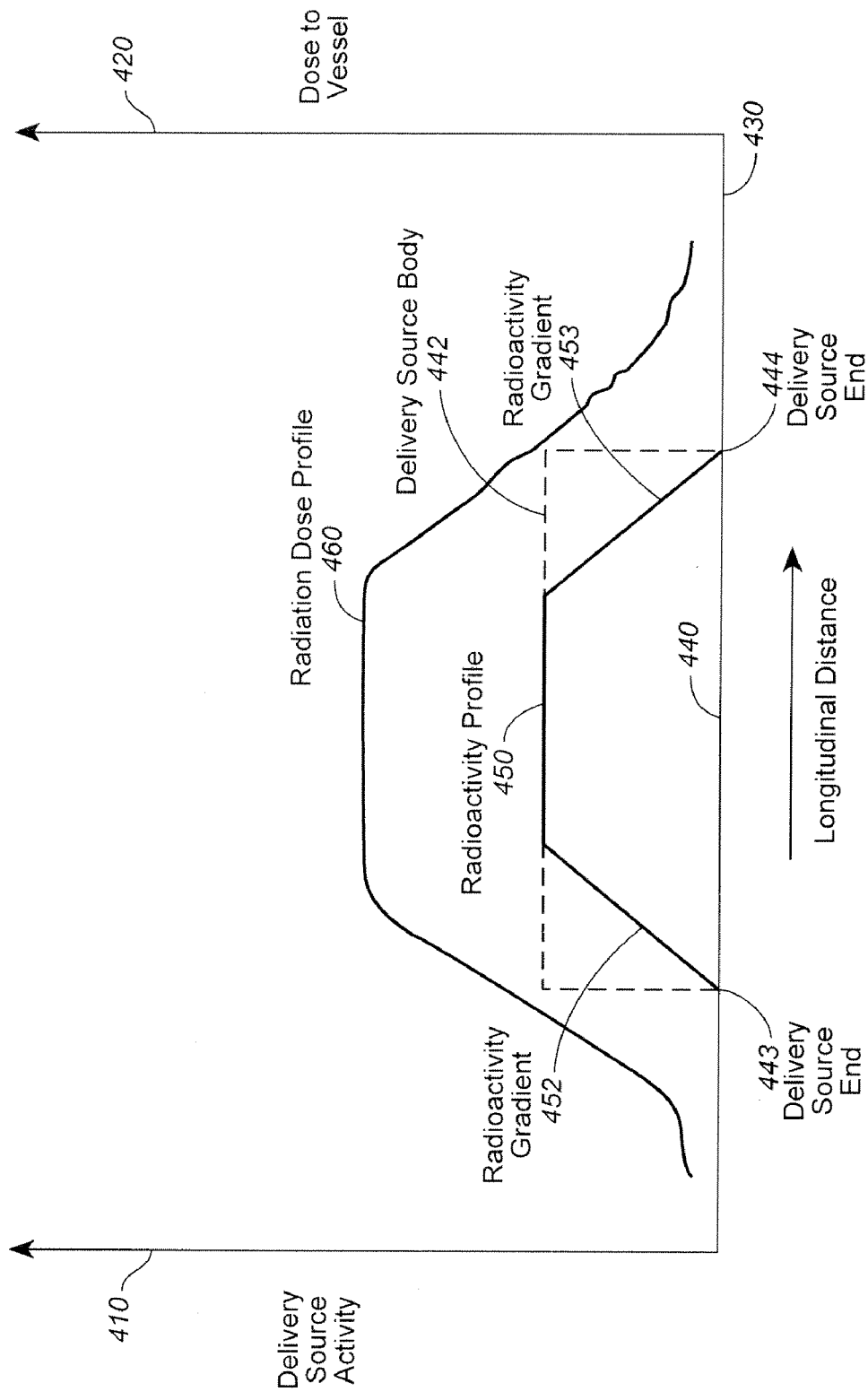
FIG. 4 is a graphical representation of an exemplary radiation dose profile of one embodiment of a radiation delivery source.

FIG. 4 shows a graphical representation of an exemplary radiation dose profile corresponding to a radiation delivery source in one embodiment of the present invention. Left vertical axis 410 represents radiation delivery source radioactivity and right vertical axis 420 represents radiation dose from the delivery source to the treated vessel. Horizontal axis 430 represents the longitudinal length of the delivery source, for example, a stent. Compared to the typical dose profile exemplified in FIG. 3, FIG. 4 differs primarily in that the radiation dose profile 460 gradually transitions to no dose delivered to a vessel near ends 443 and 444 of radiation delivery source 440. This decrease in radiation dose profile 460 results from radioactivity gradients 452 and 453 near delivery source ends 443 and 444 as shown by radioactivity profile 450.

In this embodiment, radiation delivery source 440 has two radioactivity levels as shown by radioactivity profile 450. The first radioactivity level corresponds to a therapeutic level of radiation and is typically localized near the central portion of delivery source 440. The therapeutic level may be the amount of radiation required to treat vessel wall. For example, the effective treatment of lesions on a vessel wall may require a minimum threshold level of radiation.

As the therapeutic radioactivity level reaches ends 443 and 444 of radiation delivery source 440, the radioactivity level gradually declines to a second, non-therapeutic radioactivity level in which no radiation is emitted near delivery source ends 443 and 444. The gradual decline in radioactivity over at least a portion of the longitudinal length of the delivery source 440 are gradients 452 and 453. Dashed line segment 442 shows that radioactivity gradient 452 terminates near ends 443 and 444 of delivery source 440. Radioactivity is not at the therapeutic level near ends 443 and 444 of delivery source 440. Consequently, radiation dose profile 460 shows the dose to the vessel gradually declining near delivery source ends 443 and 444.

Although the graphical profile in FIG. 4 suggests a constant decrease in radiation dose toward delivery source ends, the rate may vary according to how the delivery source is activated. For example, in another embodiment of the present invention, the delivery source may be activated such that the radiation level decreases at an exponential rate rather than at a constant rate (not shown).

Figure 5:
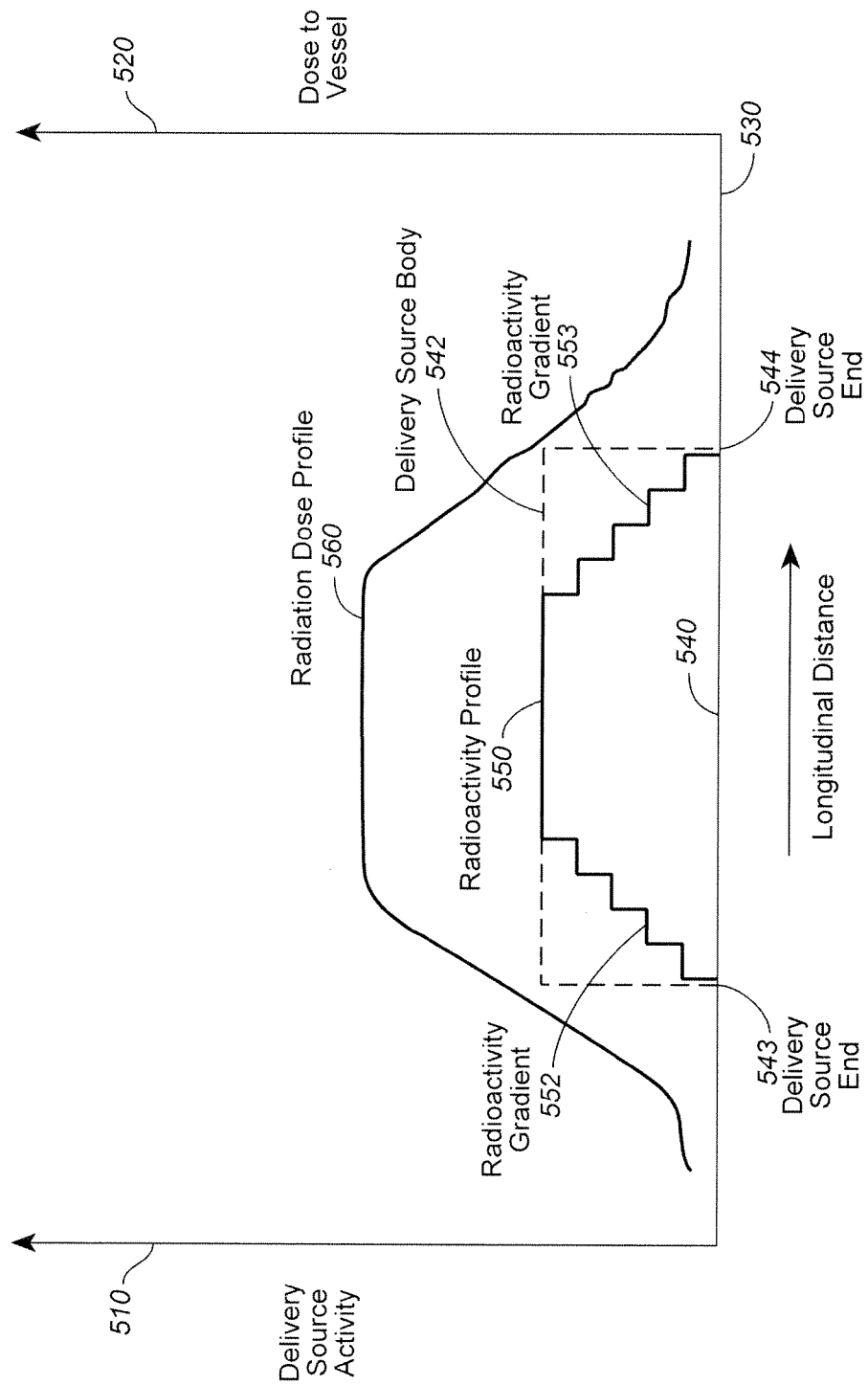
FIG. 5 is a graphical representation of an exemplary radiation dose profile of one embodiment of a radiation delivery source.

FIG. 5 shows a graphical representation of an exemplary radiation dose profile of another embodiment of a radiation delivery source. Left vertical axis 510 represents radiation delivery source radioactivity and right vertical axis 520 represents radiation dose from the delivery source to the treated vessel. Horizontal axis 530 represents the longitudinal length of the delivery source. Radioactivity profile 550 shows radioactivity gradients 552 and 553 formed as a series of declining radioactivity steps from a therapeutic level localized near the central portion of delivery source 540. Gradients 552 and 553 have incremental segments of uniform radioactivity that decreases towards the ends of the delivery source to a non-therapeutic level. Dashed line segment 542 shows that radioactivity gradients 552 and 553 near delivery source ends 543 and 544. The corresponding dose profile 560 generally follows radioactivity profile 550, in which the radiation dose gradually declines near delivery source ends 543 and 544 as a result of radioactivity gradients 552 and 553. The treated vessel experiences a gradual transition from radiation dose to no dose. This decreasing dosage effect prevents or inhibits excessive cell proliferation at the delivery source ends.

A gradual decrease in activity level in the form of a gradient that starts before the end of the delivery source allows for a transition from radiation treatment to non-treatment areas. The maximum radiation dose is typically localized at the center portion of the radiation delivery source.

Figure 6:
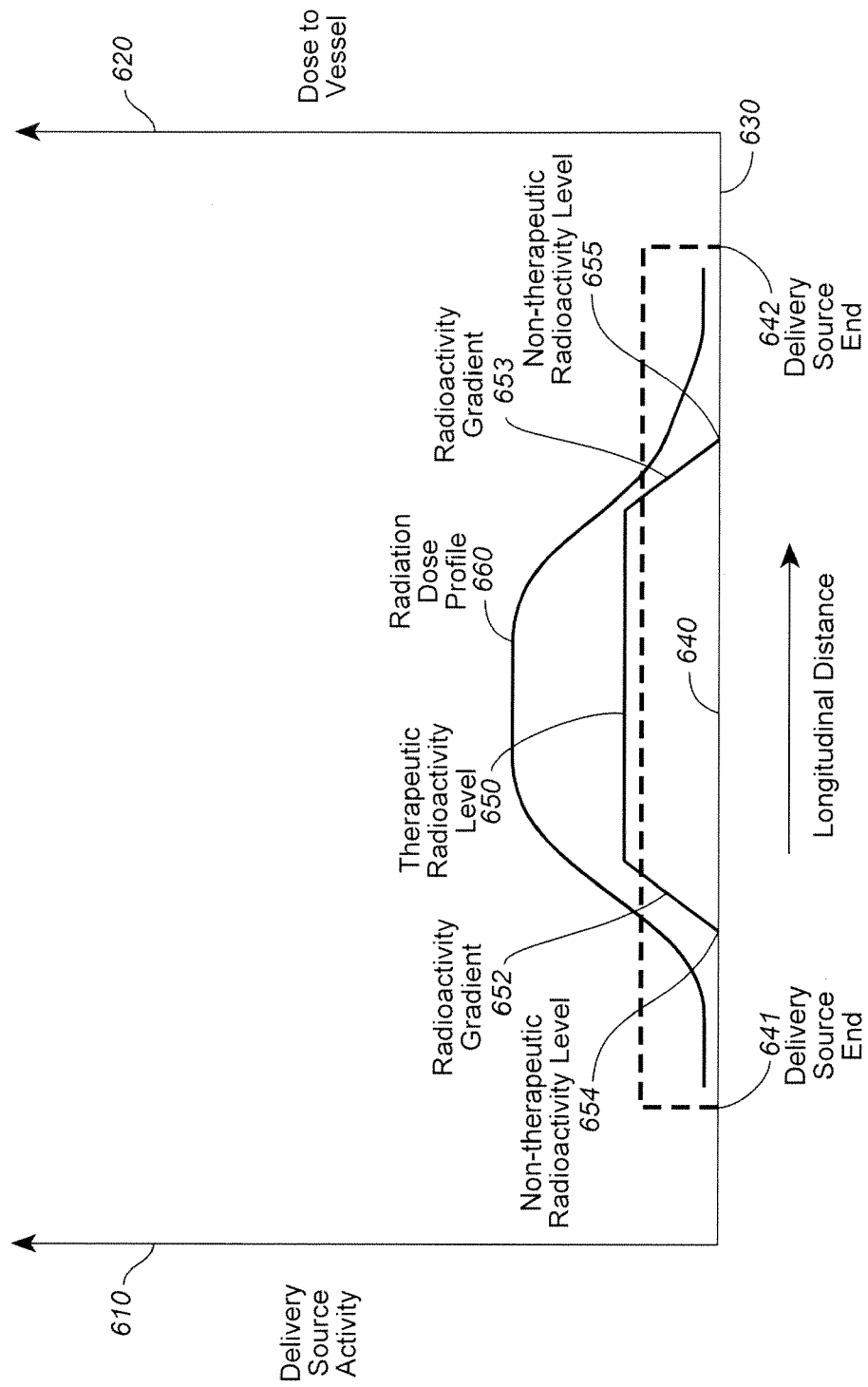
FIG. 6 is a graphical representation of an exemplary radiation dose profile of one embodiment of a radiation delivery source.

FIG. 6 shows another graphical representation of an exemplary radiation dose profile of one embodiment of a radiation delivery source. This embodiment also shows radiation dose profile 660 resulting from radiation delivery source 640 having radioactivity gradients 652 and 653. Left vertical axis 610 represents radiation delivery source radioactivity and right vertical axis 620 represents radiation dose from the delivery source to the treated vessel. Horizontal axis 630 represents the longitudinal length of the delivery source.

In this embodiment, radioactive region 680 on delivery source 640 does not cover the entire longitudinal length of delivery source 640. A uniform radioactivity level is localized at the center of delivery source 640. This level is the therapeutic radioactivity level 650 for treating a lesion in a vessel. The therapeutic activity level transitions before ends 641 and 642 of delivery source 640, decreasing to non-therapeutic radioactivity levels 654 and 655. In this embodiment, non-therapeutic radioactivity levels are zero. In another embodiment, the non-therapeutic radioactivity levels may be close to zero. Radioactivity gradients 652 and 653 terminate short of delivery source ends 641 and 642. In this embodiment, radioactivity gradients combined with zero radioactivity levels before or near the stent ends may minimize or prevent the candy-wrapper effect. This embodiment presents an alternative gradient of dosage transitioning from a therapeutic level to a non-therapeutic level to inhibit cell proliferation near the stent ends.

There are many sources for delivering radiation to tissue including, but not limited to, balloon-expandable stents, self-expandable stents, balloon catheters, source wires, guidewires and catheters. Activating the delivery source with radioactive isotopes may depend on the type of treatment desired, but beta and gamma emitting isotopes are typically used. Radiation from a beta-emitting radioisotope diminishes rapidly with distance from the source thereby delivering minimal energy at more than two millimeters. A gamma-emitting isotope may provide greater penetration and may improve dose homogeneity. Examples of gamma-emitting isotopes that may be utilized for the present invention include Cesium 137 (137Cs), Palladium 103 (103Pd), Iridium 192 (192Ir) and Ruthenium 106 (106Ru). Examples of beta-emitting isotopes include Phosphorous 32 (32P), Yttrium 90 (90Y), and Vanadium 48 (48V). The appropriate activity level for treatment may be measured by the corresponding dose levels associated with the particular isotope. Radiation doses for treatment are typically referenced as the cumulative dosage up to two millimeter tissue depth after 30 days. Accordingly, activity levels may vary with isotopes.

Alternatively, a combination of isotopes may be used to activate a delivery source. In some cases, two or more types of beta or gamma emitting isotopes, or a combination of beta and gamma emitting isotopes may be used to activate a radiation delivery source. For example, an activated stent may have gamma isotopes at the center and a gradient of beta isotopes at the ends.

Radioactivity levels typically may vary according to isotope or isotopes used, time of exposure, configuration of delivery source, type of delivery source, and lesion depth. Because the radiation dose received by a vascular lesion may be the controlling factor, radioactivity levels are calculated to meet the desired dose. The therapeutic treatment dose may be up to 60 Gray, with a preferable dose range of 3 to 30 Gray at a tissue depth of up to approximately 2 millimeters. The dose time may be a few minutes for a source wire and several weeks for a stent. For example, the radioactivity for a phosphorous 32 stent from the time of vascular placement, with a total radiation dose delivered over the lifetime of radioactivity, would be approximately 0.3 to 2.0 micro-Curie per millimeter of stent length. A phosphorous 32 source wire, with a total radiation dose delivered over minutes, would have a radioactivity of approximately 10 to 200 milli-Curie.

Delivery source activation may be accomplished through various techniques known in the art, including masking and selective activation, modified to achieve a radioactivity gradient. Ion beam implantation and plasma ion implantation are examples of selective ion processes.

In ion beam implantation, an isotope is first converted into a gas. The gaseous isotope is ionized and injected into an ion beam accelerator where the ions are accelerated to speeds close to the speed of light. The radioactive ions are focused into a beam and accelerated to the target stent at energies high enough to imprint the ions to the delivery source surface. The high negative bias accelerates the isotope and implants the ions onto the exposed surfaces of the stent. For example, a stent is spun at a constant rate while an ion beam travels back and forth longitudinally along the surface of the stent. The amount of radioactive ions on the stent may depend on how long the beam targets a particular area of the stent. Thus, by gradually decreasing the beaming time near the ends of the stent, a radioactivity gradient may be achieved.

In plasma ion coating, the delivery source is placed in the ion source itself. High negative voltage pulses accelerate the isotope in the plasma and implants the ions onto the exposed surface of the delivery source. Radioactive shielding "masks" on the delivery source prevent covered regions from being activated with ions. Changing the positioning of the "masks" between implantation procedures allows for the creation of gradients.

In another embodiment radioactivity gradients on stent ends may be formed by gradually narrowing the struts near the end regions compared to wider struts in the central region. In doing so, there is less surface area for implanting radioactive isotopes near the stent ends, thereby lowering radioactivity.

The length of radiation delivery sources, whether stents or source wires with radioactive regions at the distal end, may vary according to the target lesion size and length. For stents, the length may be selected to exceed lesion length. In this type of stent, the radioactivity gradients on the stent may begin at a point near or past the lesion ends so that the entire lesion is treated at the therapeutic dose level. The gradient keeps the non-lesion tissue exposed to the radiation from responding with significant tissue growth, although some tissue response may be expected. The gradient length may also vary. A longer gradient may be necessary with gamma-emitting isotopes due to their higher penetrating effects compared to beta-emitting isotopes. Alternatively, an optimum gradient length may be linked to a particular isotope irrespective of stent length.

Radiation delivery sources, such as stents and source wires may be made from a variety of materials commonly known in the art. For example, balloon-expandable stents may be made of stainless steel. Other metals that may be used include cobalt chromium, tantalum, gold, nickel titanium alloys or other similar composites. Comparable metals may be used to make source wires as well.

Short Transitional Edge Protection (STEP™) technology is described in U.S. Pat. No. 5,470,313, issued to Crocker et al., and licensed by Advanced Cardiovascular Systems, Inc. of Santa Clara, Calif. Combining STEP™ technology with an activity gradient of the present invention may provide an additional therapeutic benefit for radioactive stent application. STEP™ technology incorporates a unique balloon design, which creates a step-shaped taper or shoulder at each end of the stent to reduce the amount of balloon material outside the stent. This optimal stent and balloon configuration minimizes the amount of vessel dilated by the balloon beyond the ends of the stent. It also enables uniform stent expansion during deployment and implantation.

With balloon-expandable, radioactive stents, STEP™ technology may be used to minimize vessel injury to areas beyond the ends of the stent, because the STEP™ balloon may not contribute any physical injury to regions beyond the ends of the stent. Thus, a radioactivity gradient near the ends of the stent to minimize tissue damage from radiation, combined with a STEP™ balloon to minimize physical damage at stent ends may further reduce the likelihood of candy-wrapper or edge effect.

Figure 7:
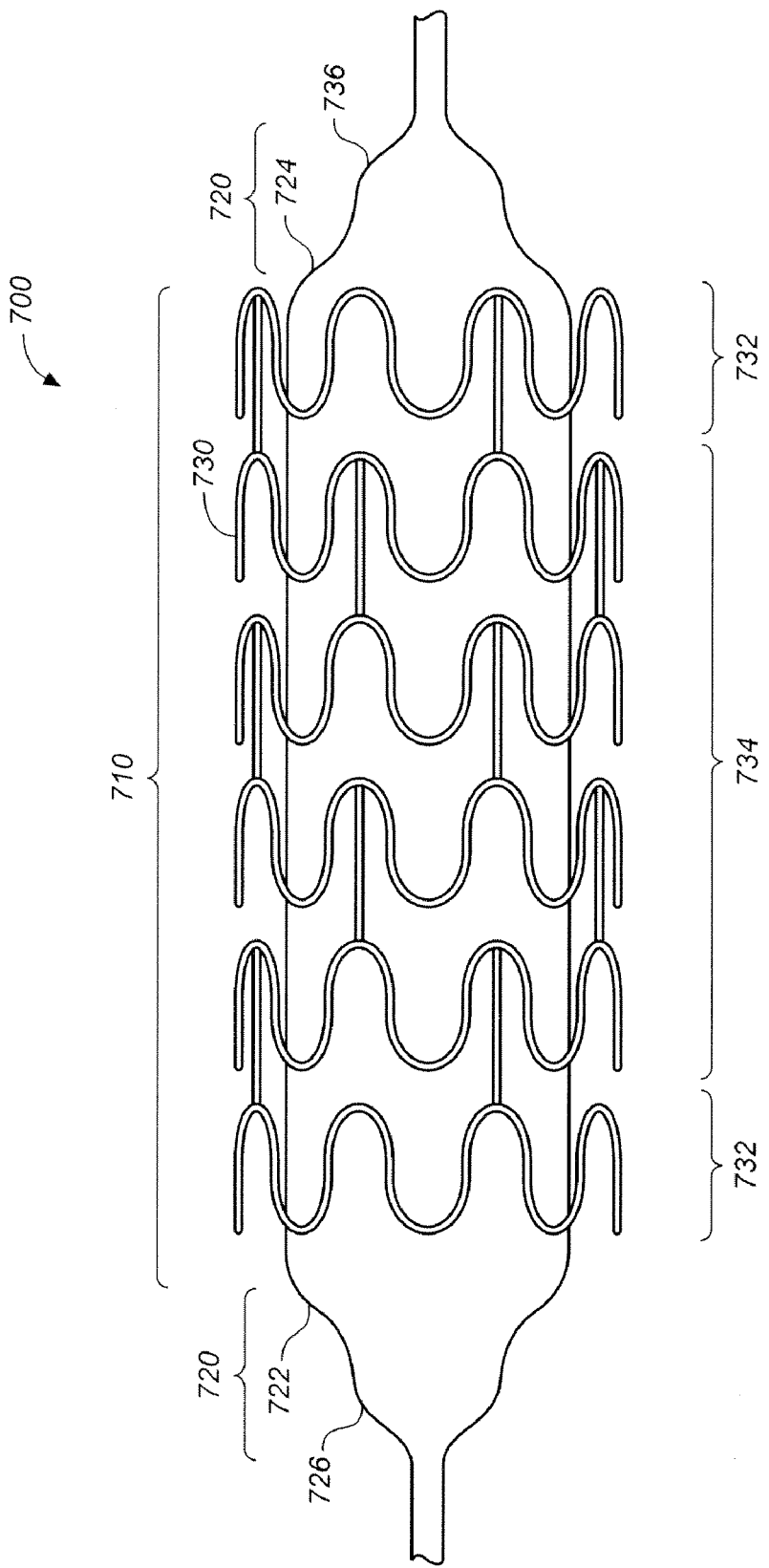
FIG. 7 is a side view of a radiation delivery source in the form of a stent expanded by a balloon having Short Transitional Edge Protection (STEP™) technology.

FIG. 7 shows an embodiment of a radioactive stent with a gradient of the present invention mounted on a STEP™ balloon. Balloon 700, which includes central portion 710 that is inflatable to a generally cylindrical shape, also has at least one stepped shoulder portion 720 that extends longitudinally from central portion 710. Stepped shoulder portion or portions 720 have a frustoconical shape narrowing away from central portion 710. Shoulders 722 and 724 form part of stepped shoulder portions 720. Stepped shoulder portions 720 may further include a generally cylindrical sections 726 and 736 extending from the narrowest point of each frustoconical stepped shoulder portion 720. Stent 730 is crimped on balloon 700. Stent 730 has edge portions 732 that are coterminous with central portion 710 of balloon 700.

Stent 730 has a radioactive region thereon. A therapeutic radioactivity level is localized near central portion 734 of stent 730. A gradient of decreasing radioactivity to a non-therapeutic radioactive level starts at a point near edge portions 732 toward the ends of stent 730.

While radioactivity gradient embodiments have been described in connection with stents as radiation delivery sources, it should be noted that the present invention is not necessarily so limited. The benefits of utilizing radioactivity gradients are applicable to alternative sources of radiation delivery. Any type of radiation source, such as radioactive source wires or radioactive guidewires, for example, may present the risk of cell proliferation at the region where healthy cells are exposed to radiation.

Drug delivery sources also may present the possibility for edge effects. For example, drug delivery catheters may induce edge effect responses around regions where healthy tissue cells in a vessel are exposed to medication. In addition, drugs delivered on stent platforms may be potent enough to destroy endothelial cells lining the vessel wall. Drug concentration gradients may minimize or prevent proliferation of unwanted cells at or near the treatment ends, as well as allowing endothelial cells to survive at the treatment ends. The surviving endothelial cells could migrate towards the center of the treatment area to replenish the endothelial cells.

Figure 8:
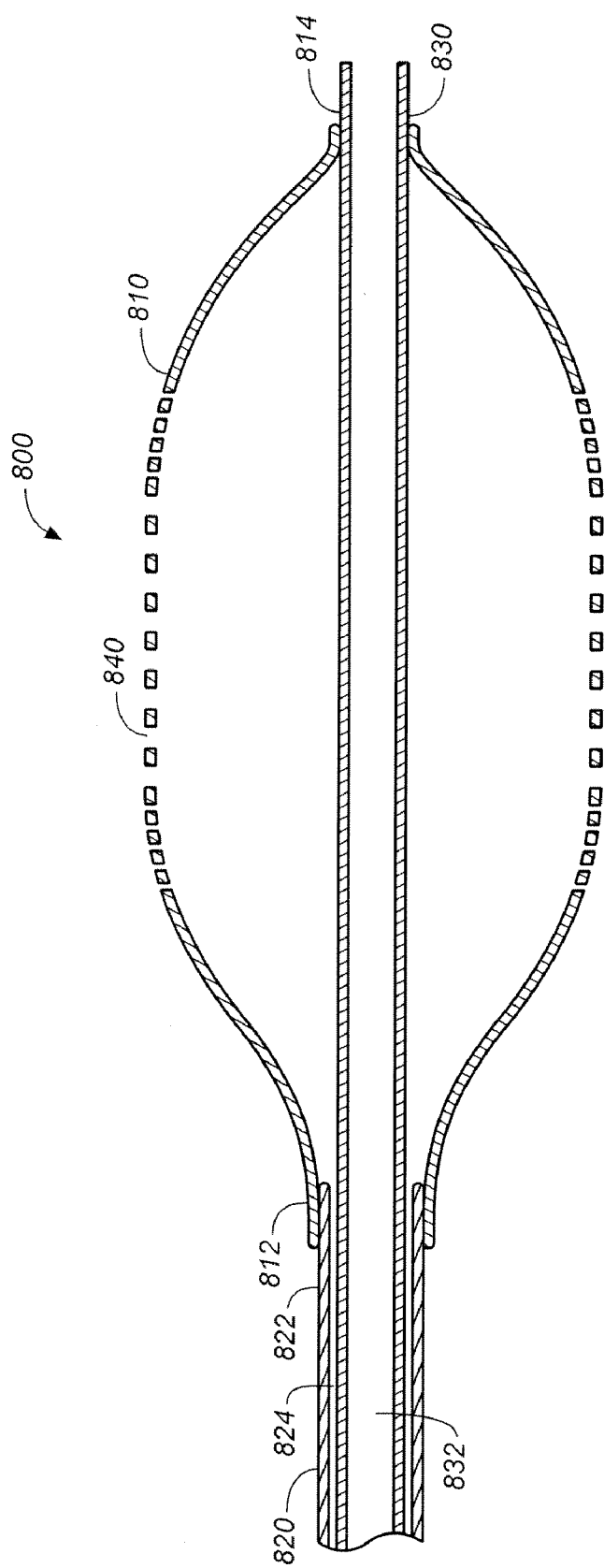
FIG. 8 is a cross-sectional, side view of one embodiment of the present invention in which a drug delivery source in the form of a drug-eluting balloon catheter has pores to release gradients of drug concentrations.

FIG. 8 shows a cross-sectional, side view of an embodiment of the present invention. FIG. 8 shows a drug delivery source in the form of drug-eluting balloon catheter 800. Balloon 810 is attached near distal end 822 of catheter 820. Proximal end 812 of balloon 810 is attached to catheter 820, and distal end 814 is attached to the outer surface of inner guiding tube 830. Guiding tube 830 extends within catheter 820 and past distal end 822 of catheter 820. Guiding tube 830 has lumen 832 through which a guidewire (not shown) extends to position balloon 810 in a vessel.

Balloon 810 has pores 840 distributed throughout its surface. As pressure is applied through outer lumen 824 of catheter 820 to inflate balloon 810, a therapeutic drug is also released through pores 840. Pores 840 may vary in size and distribution to control the concentration of a drug released to a vessel. Pores 840 may be holes through the wall of balloon 810. Alternatively, individual micro-needles may be inserted through holes in the balloon wall to create pores 840 (not shown). These and other types of pores known in the art may be substituted.

Figure 9:
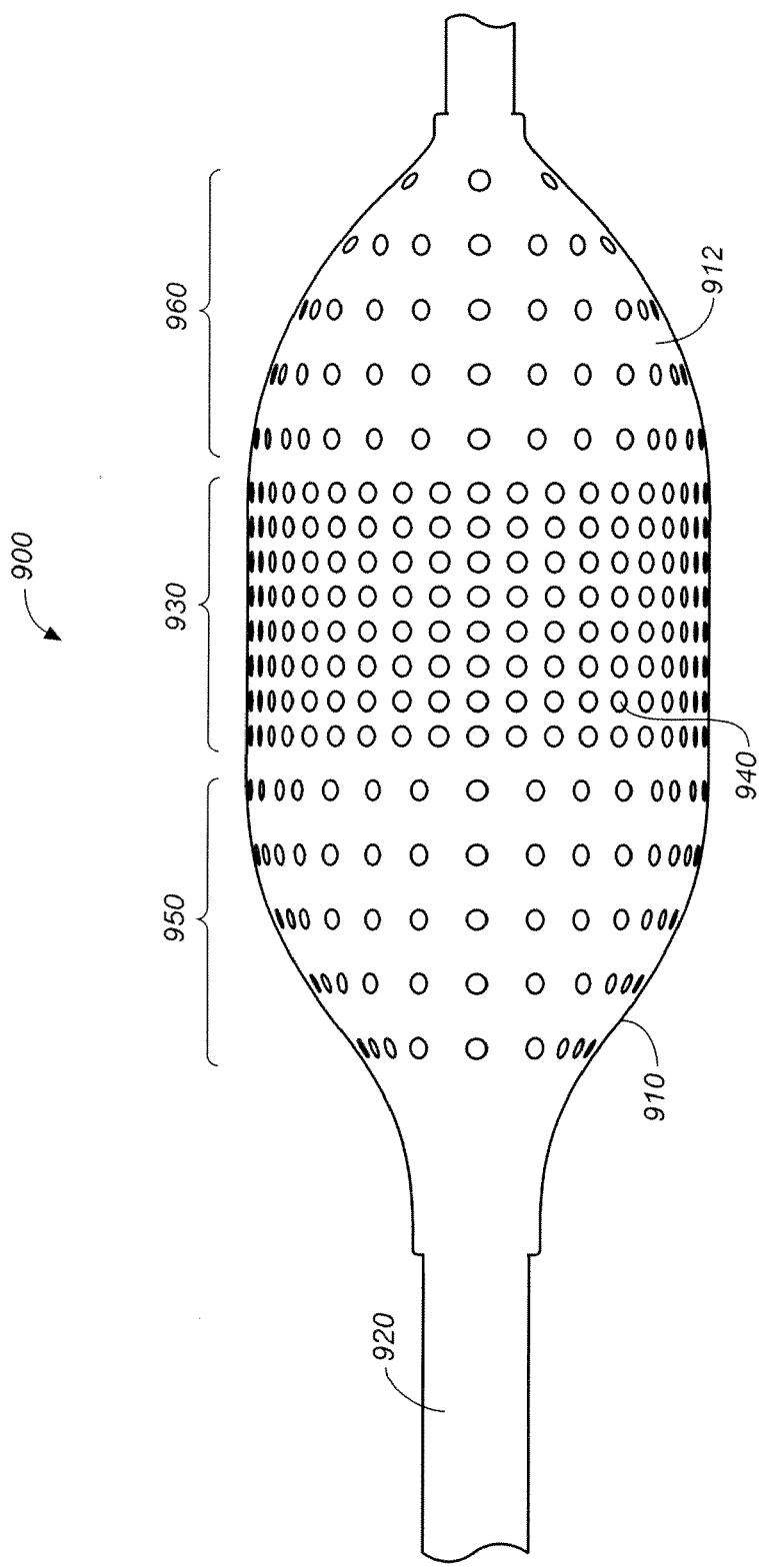
FIG. 9 is a side view of one embodiment of the present invention in which a drug delivery source in the form of a drug-eluting balloon catheter has fewer pores near the ends of the balloon to create concentration gradients.

FIG. 9 is a side view of another embodiment of the present invention for drug-eluting balloon catheter 900. Balloon 910, in an inflated state, is shown attached to catheter 920. Pores 940 are distributed throughout surface 912 of balloon 910. Central portion 930 of balloon 910 has a uniform distribution of pores 940. Near proximal end 950 and distal end 960 of balloon 910, the distribution of pores 940 gradually decreases such that the number of pores per unit surface area decreases to provide the gradient of drug concentration.

This embodiment of a drug-eluting balloon catheter shows a gradient of drug concentrations formed through pores 940. The number of pores 940 near central portion 930 is evenly distributed. Consequently, the concentration of a drug released through pores 940 from central portion 930 is uniform so that a vessel receives a concentration corresponding to a therapeutic dose level. The number of pores 940 distributed from central portion 930 to proximal end 950 and to distal end 960 gradually decrease so that a concentration corresponding to a non-therapeutic dose is received by a vessel near proximal end 950 and distal end 960. This gradual reduction in the number of pores 940 creates a concentration gradient as a drug is released through pores 940.

Figure 10:
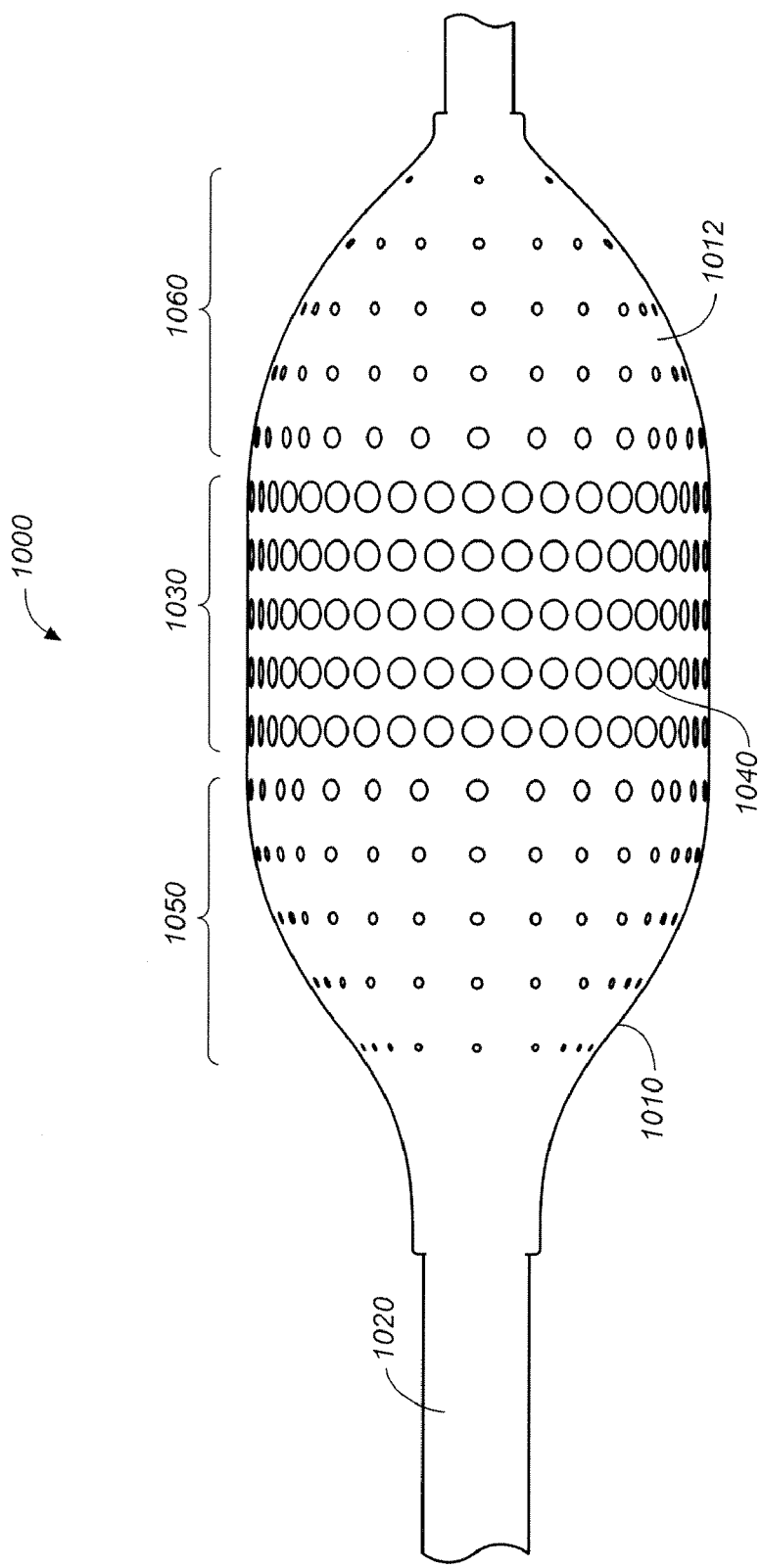
FIG. 10 is a side view of one embodiment of the present invention in which a drug delivery source in the form of a drug-eluting balloon catheter has smaller pores near the ends of the balloon to create concentration gradients.

FIG. 10 shows another variation of pores on a balloon to create a concentration gradient. FIG. 10 is a side view of another embodiment of drug-eluting balloon catheter 1000. Balloon 1010, in an inflated state, is shown attached to catheter 1020. Again, pores 1040 are distributed throughout surface 1012 of balloon 1010.

In this embodiment, pores 1040 near central portion 1030 are uniformly sized. This allows for a uniform concentration of a drug to be released through pores 1040. This uniform concentration may correspond to a therapeutic dose received by a vessel. Pores 1040 distributed from central portion 1030 to proximal end 1050 and distal end 1060 gradually decrease in size. This gradual reduction in pore size creates a concentration gradient as a drug is released from central portion 1030 to proximal end 1050 and distal end 1060.

Figure 11:
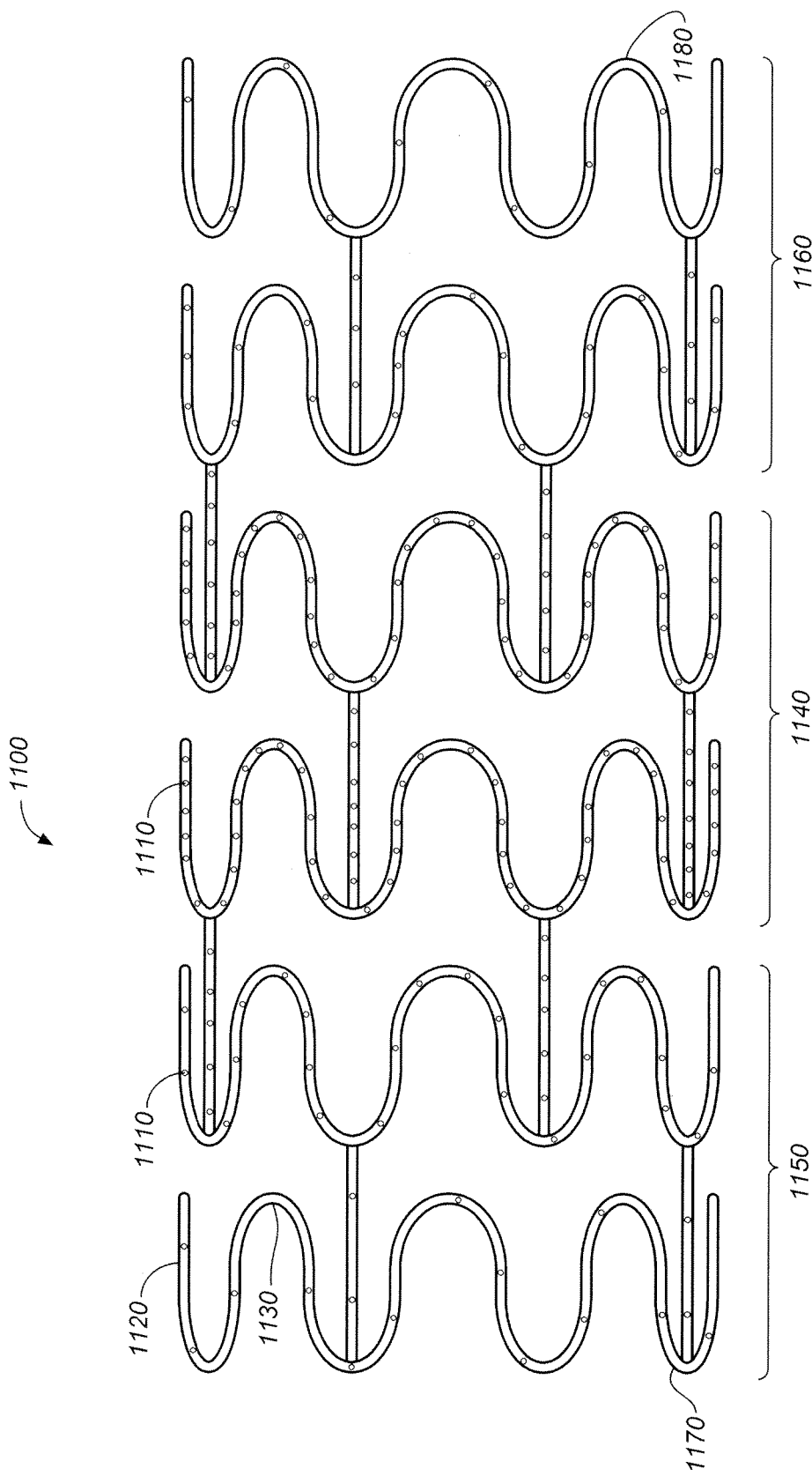
FIG. 11 is a side view of one embodiment of the present invention in which a drug delivery source in the form of a stent has indentations to accommodate a drug.

Drug delivery sources are not limited to drug-eluting balloon catheters. In one embodiment, a drug delivery source may be an intravascular stent. FIG. 11 shows a side view of a drug delivery stent having concentration gradients. Stent 1100 has indentations 1110, often referred to as micro-depot indentations, formed in surface 1120 of struts 1130. A laser cutting technique is preferably used to cut indentations 1110.

Stent 1100 has a drug delivery region thereon. Indentations 1110 accommodate a drug to form the drug delivery region along surface 1120 of stent 1100. Central portion 1140 on stent 1100 has a uniform distribution of indentations to accommodate a uniform drug concentration to provide a therapeutic drug dose level to a vessel. Regions of drug concentration gradients 1150 and 1160, gradually decreasing to a non-therapeutic drug dose, start at a point inward of proximal end 1170 and distal end 1180 of stent 1100.

Gradient regions 1150 and 1160 may be formed by gradually decreasing the distribution of indentations toward proximal end 1170 and distal end 1180 from central portion 1140 of stent 1100. In another embodiment, gradient regions 1150 and 1160 may be formed by gradually decreasing the size of the indentations toward proximal end 1170 and distal end 1180.

Drug delivery stents may be coated with a drug. Methods for coating drug delivery sources with a particular drug are well known in the art. A drug may be coated on a stent, for example, by dipping or spraying a drug-laced polymer on the stent.

In stent dipping, the stent is submersed in a drug compound that adheres to the stent. A series of masking steps in conjunction with the dipping process creates a gradient coating thickness.

In stent spraying, a drug liquid compound to be applied to the stent is atomized as the compound passes through a nozzle at high pressures. The stent is passed in front of the nozzle where the compound adheres to the stent. Spray coating may be performed at variable translational speeds to achieve a gradient coating concentration or thickness. Spray coating may also be performed using multiple drug mixtures through a single nozzle. The pressure for each mixture converging on the nozzle may be varied such that the drug concentration of the final mixture is increased or decreased as desired. The final concentration is controlled to coincide with the translation with respect to the stent in order to achieve the gradient drug concentrations.

A variety of drugs may be delivered from stent and catheters systems to a vessel utilizing a concentration gradient. Examples of classes of drug compounds include, but are not limited to, anti-inflammatory, anti-proliferative, anti-migratory, inhibitors of matrix or collagen deposition, and apoptosis inducers.

While drug concentration gradient embodiments have been described in connection with balloon catheters and stents, one skilled in the art will appreciate that the present invention is not necessarily so limited. The benefits of utilizing drug concentration gradients are applicable to alternative sources of drug delivery. Any type of drug source may present the risk of cell proliferation at the region where healthy cells are exposed to anti-cell proliferation drugs.

A method to make radioactive a radiation delivery source such as a stent or source wire having radioactivity gradients is presented. The stent or source wire is coated with beta, gamma, or a combination of beta and gamma emitting isotopes such that a radioactive region is formed. Ion beam implantation, plasma ion implantation or other ion implantation techniques common in the art may be used to coat the stent or source wire. The radiation delivery source has a therapeutic radioactivity level localized between the proximal end and the distal end of stent or source wire. Radioactivity gradients begin near the proximal end and the distal end of the delivery source in which the radioactivity decreases from the therapeutic radioactivity level to a non-therapeutic activity level. The gradient may be of variable length and rate.

A method to make a drug region including drug concentration gradients on an intravascular drug delivery source, such as a stent or drug-eluting balloon catheter, is presented. Dipping or spray coating techniques common in the art may be used to coat the drug delivery source. Alternatively, pores of decreasing size and distribution may be created on a balloon catheter to elute drugs. A therapeutic concentration of a drug is localized between a proximal end and a distal end of the delivery source. The coating techniques are modified to create drug concentration gradients near the proximal end and distal end of the delivery source. The gradients transition the drug concentration from a therapeutic concentration level to a non-therapeutic concentration level. For drug eluting catheters, uniformly sized pores are created in a central area of the catheter. Near the proximal and distal end of the catheter, the pore sizes gradually decrease to reduce the amount of a drug released through the pores. For stents, indentations may be formed on the surface the stent to accommodate a drug. The distribution of indentations may be gradually decreased towards the ends of the stent to create concentration gradients.

What is claimed is:

1. An apparatus to deliver a therapeutic agent to a vessel, comprising:
    an elongated source of a therapeutic agent, the source having an amount or a concentration of the therapeutic agent that gradually decreases along a length of the elongated source from a location inward of a proximal end or at the proximal end of the elongated source, or from a location inward of a distal end or at the distal end of the elongated source.

2. The apparatus of claim 1 wherein the source comprises a drug delivery stent having an anti-cell proliferation drug for treatment of the vessel.

3. The apparatus of claim 1 wherein the source comprises a radioactive intravascular stent or a drug delivery stent.

4. An apparatus for delivering therapeutic radiation to a vessel, comprising:
    an elongated radiation delivery source including a radioactive region thereon, the radioactive region having a proximal end and a distal end, and being capable of delivering a therapeutic level of radioactivity, wherein the radioactive region includes a segment gradually transitioning from the therapeutic level to a non-therapeutic level of radioactivity at the proximal end or the distal end of the radioactive region.

5. The apparatus of claim 4 wherein the radioactive region comprises a beta particle emitting isotope.

6. The apparatus of claim 4 wherein the radioactive region comprises a gamma particle emitting isotope.

7. The apparatus of claim 4 wherein the radiation delivery source comprises an intravascular stent.

8. The apparatus of claim 4 wherein the radioactive region comprises a beta particle and a gamma particle emitting isotope.

9. An intravascular stent for delivering therapeutic radiation to a vessel, comprising:

a radioactive region along an elongated length of a stent, the radioactive region having an area capable of delivering a substantially uniform dose of radioactivity to a vessel localized at a central portion of the stent, wherein the radioactive region includes a radioactivity gradient at a proximal end or a distal end of the radioactive region, the radioactivity gradient gradually decreasing the dose delivered to the vessel from a therapeutic level to a non-therapeutic level of radioactivity, and wherein the gradient decreases the dose from a location inward of the proximal end or at the proximal end, or decreases the dose from a location inward of the distal end or at the distal end of the radioactive region.

10. The stent of claim 9 wherein the radiation dose delivered to the vessel inhibits vessel cell proliferation along the elongated length of the stent and past the proximal end or the distal end of the stent.

11. The stent of claim 9 wherein the area capable of delivering the substantially uniform level of radioactivity comprises a greater longitudinal length than the gradient.

12. The stent of claim 9 wherein the gradient comprises a uniform rate of decrease of radioactivity level.

13. The stent of claim 9 wherein the gradient comprises a variable rate of decrease of radioactivity level.

14. The stent of claim 9 wherein the gradient comprises a decrease of radioactivity level by incremental steps.

15. The stent of claim 9 wherein the radioactive region comprises a beta particle emitting isotope.

16. The stent of claim 9 wherein the radioactive region comprises a gamma particle emitting isotope.

17. The stent of claim 9 wherein the radioactive region comprises a beta and a gamma emitting particle isotope.

18. The stent of claim 9 wherein the dose of radioactivity comprises up to 60 Gray.

19. An intravascular stent for delivering a drug to a vessel, comprising:

a drug delivery region along an elongated length of a stent, the drug delivery region having a variable drug concentration thereon, wherein the drug delivery region includes an area of substantially uniform drug concentration localized at a central portion of the stent, and wherein the drug delivery region includes a drug concentration gradient at a proximal end or a distal end of the drug delivery region, the drug concentration gradient gradually decreasing from a therapeutic dose level to a non-therapeutic dose level, and wherein the gradient decreases from a location inward of the proximal end or at the proximal end, or decreases from a location inward of the distal end or at the distal end of the drug delivery region.

20. The stent of claim 19 wherein a drug dose delivered to the vessel inhibits vessel cell proliferation along the elongated length of the stent and past the proximal end or the distal end of the stent.

21. The stent of claim 19, wherein the drug delivery region contains a drug selected from the group consisting of an anti-inflammatory compound, an anti-proliferative compound, an anti-migratory compound, an inhibitor of matrix or collagen deposition, and an apoptosis inducer.

* * * * *